United States Patent [19]

Tonari et al.

[11] Patent Number: 4,863,587
[45] Date of Patent: Sep. 5, 1989

[54] METHOD FOR RECOVERY OF A PHENOLIC POLYMERIZATION INHIBITOR

[75] Inventors: Takashi Tonari; Yasuhiko Ikeda, both of Oita, Japan

[73] Assignee: Nippon Steel Chemical Co., Ltd., Tokyo, Japan

[21] Appl. No.: 171,372

[22] Filed: Mar. 21, 1988

[30] Foreign Application Priority Data

Mar. 19, 1987 [JP] Japan .................................. 62-62492

[51] Int. Cl.$^4$ ....................... C07C 37/68; C10G 17/00
[52] U.S. Cl. .................................... 208/263; 208/321; 208/333; 203/9; 203/56; 585/835
[58] Field of Search ............... 208/311, 312, 321, 333, 208/348, 263; 585/835, 836; 203/9, 56

[56] References Cited

U.S. PATENT DOCUMENTS

| | | | |
|---|---|---|---|
| 2,304,728 | 12/1942 | Boyer . | |
| 2,486,342 | 10/1949 | Taylor et al. | 203/56 X |
| 2,526,567 | 10/1950 | Drake et al. . | |
| 2,655,462 | 10/1953 | Morfit | 208/321 |
| 2,769,707 | 11/1956 | Fierce et al. | 208/263 |
| 3,632,626 | 1/1972 | Schneller . | |
| 3,959,395 | 5/1976 | Higgins . | |
| 4,033,829 | 7/1977 | Higgins . | |
| 4,349,415 | 9/1982 | DeFilippi et al. | 208/339 |
| 4,406,780 | 9/1983 | Gould et al. | 208/263 |

FOREIGN PATENT DOCUMENTS 2158380 6/1973 France .
1403417 8/1975 United Kingdom .

Primary Examiner—Glenn Caldarola
Attorney, Agent, or Firm—Burns, Doane, Swecker & Mathis

[57] ABSTRACT

A phenolic polymerization inhibitor is recovered from a styrene distillation residue containing the phenolic polymerization inhibitor by a method which comprises extracting the inhibitor from the styrene distillation residue with an oxygen-containing organic solvent having not more than 6 carbon atoms, adding an aromatic hydrocarbon solvent to the oxygen-containing organic solvent phase consequently obtained, and subjecting the resultant mixture to distillation thereby separating the mixture into a solution of the phenolic polymerization inhibitor in the aromatic hydrocarbon solvent and the oxygen-containing organic solvent. The recovered solution is put to use as a polymerization inhibitor either in the unmodified form or in a form separated from the aromatic hydrocarbon solvent.

19 Claims, 1 Drawing Sheet ns bearing other substituents are also usable. The styrene tar and dissolve it only sparingly. Among other aromatic hydrocarbon solvents mentioned above, toluene and xylene prove particularly desirable.

METHOD FOR RECOVERY OF A PHENOLIC POLYMERIZATION INHIBITOR

BACKGROUND OF THE INVENTION

1. Field of the Invention

This invention relates to a method for the recovery of a polymerization inhibitor and more particularly to a method for the recovery of a phenolic polymerization inhibitor from a styrene distillation residue.

2. Description of the Prior Art

In the refinement by distillation of a material containing a vinyl aromatic compound such as styrene or vinyl styrene, there is followed the practice of adding to the material a phenolic polymerization inhibitor for the purpose of precluding the material from undergoing polymerization during the course of distillation. In such case, the polymerization inhibitor accumulates in the distillation residue (hereinafter referred to as "styrene tar"). Studies devoted to the development of a technique for the recovery of the phenolic polymerization inhibitor accumulated in the styrene tar have been under way for a fairly long time to date. U.S. Pat. Nos. 3,969,395 and 4,033,829, for example, disclose a method which comprises extracting the inhibitor from a styrene tar containing dinitrophenol polymerization inhibitor with an alkaline aqueous solution, then mixing the aqueous phase of the extract with a mineral acid and an organic solvent, recovering from the resultant mixture the organic phase containing the dinitrophenol polymerization inhibitor, and reusing the organic phase as the polymerization inhibitor.

Because the above technique requires the use of an alkaline aqueous solution and a mineral acid, the operation of this technique necessitates an apparatus resistant to acids and alkalis. Further, since the above-described recovery method involves chemical reactions, it is complicated to operate.

An object of this invention, therefore, is to provide a novel method for the recovery of a polymerization inhibitor.

Another object of this invention is to provide a novel method for recovering a phenolic polymerization inhibitor from a styrene distillation residue without requiring use of any acid or alkali.

SUMMARY OF THE INVENTION

The objects described above are accomplished by a method for the recovery of a phenolic polymerization inhibitor from a styrene distillation residue containing the phenolic polymerization inhibitor, which comprises extracting the inhibitor from the distillation residue with an oxygen-containing organic solvent having not more than 6 carbon atoms, adding an aromatic hydrocarbon solvent to the resultant oxygen-containing organic solvent phase, and subjecting the resultant mixture to distillation thereby separating the mixture into an aromatic hydrocarbon solution of the phenolic polymerization inhibitor in the aromatic hydrocarbon solvent and the oxygen-containing organic solvent.

This invention recovers from the styrene distillation residue the phenolic polymerization inhibitor in the form of a solution in an aromatic hydrocarbon solvent without requiring use of any acid or alkali and, therefore, enjoys the following advantages:

(A) Since the recovery is attained without requiring any acid or alkali, (a) by-products is produced neither an acid nor an alkaline waste water, (b) the use of an apparatus resistant to against acids and alkalis is not required, and (c) an of emulsion is not formed during the course of extraction.

(B) Since the phenolic polymerization inhibitor is recovered in the form of a solute in an aromatic hydrocarbon solvent, it can be reused in its unmodified form as a polymerization inhibitor for the vinyl aromatic compound.

Another advantage of this invention is that the oxygen-containing organic solvent and the aromatic hydrocarbon solvent can be recovered and reused.

DETAILED DESCRIPTION OF PREFERRED EMBODIMENT

Figure 1:
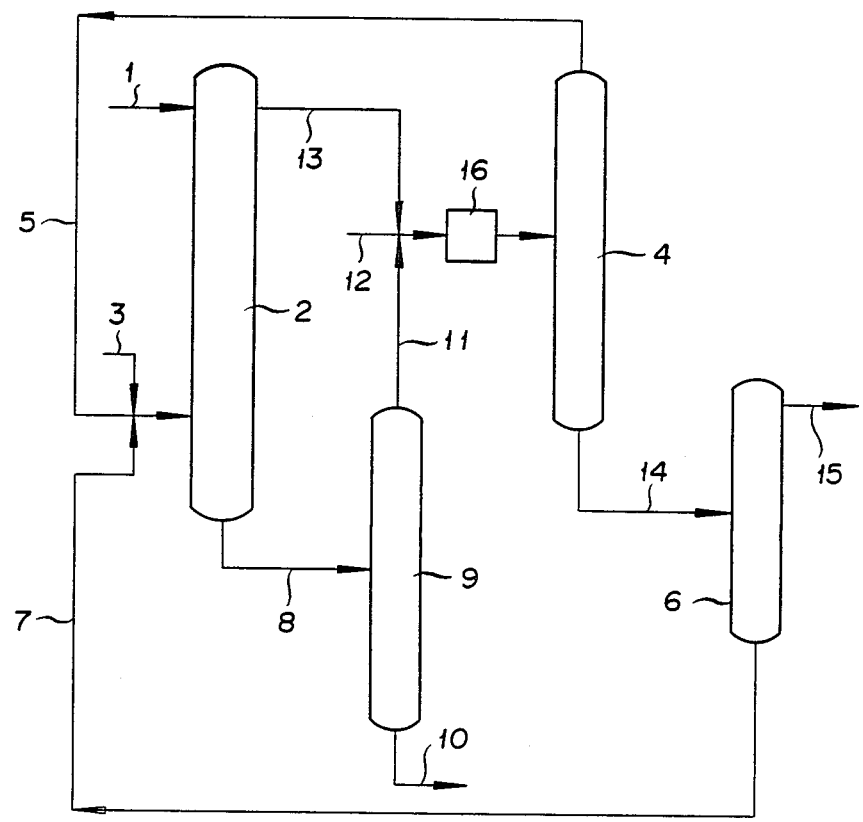
FIG. 1 is a schematic illustration of a working example of the method of this. invention.

Now this invention will be described in detail below. The term "phenolic polymerization inhibitor" as used in the present invention includes those which are widely known such as from the disclosures of U.S. Pat. Nos. 3,632,626, 2,526,567, 2,304,728 etc. As typical examples of the phenolic polymerization inhibitor, there can be cited nitrophenols such as 2,4-dinitrophenol,2,6-dinitrophenol, 2,6-dinitro-4-chlorophenol, 2-nitrophenol, 3-nitrophenol, 4-nitrophenol, 2-nitro-4-chlorophenol, 2-nitro-4-bromo6-chlorophenol, and 2-nitro-4,6-dichlorophenol, particularly dinitrophenols, dinitrocresols such as 4,6-dinitro-o-cresol, alkylbenzoquinone oximes, t-butyl catechol, hydroquinone, monomethyl ether of hydroquinone, di-t-butyl hydroquinone, 2,6-diisopropyl-o-cresol, and 3,6-dimethoxyphenol. Among other inhibitors, mononitrophenols such as nitrophenol and nitrocresol, and dinitrophenols such as dinitrophenol and dinitrocresol are particularly desirable. These compounds prevent vinyl aromatic compounds from undergoing polymerization and are more readily soluble in oxygen-containing organic solvents than in the styrenes tar.

The term "styrene" as used in the present invention refers to those compounds which are cited in U.S. Pat. No. 3,632,626 etc. They are vinyl aromatic compounds, specifically homologs and analogs of styrene such as styrene, vinyl styrene, α-methyl styrene, vinyl toluene, and chlorostyrene. The styrene distillation residue is a residue which occurs when a styrene as mentioned above is subjected, in combination with the polymerization inhibitor to purification as by distillation. The distillation residue which contains this polymerization inhibitor qualifies as the styrene tar.

The oxygen-containing organic solvent used advantageously for the sake of this invention should possess not more than 6 carbon atoms, desirably not more than 5 carbon atoms, and more desirably not more than 3 carbon atoms. If the number of carbon atoms exceeds 7, the organic solvent and the styrene tar dissolve into each other so readily as to render phase separation difficult. The oxygen contained in the organic solvent serves to lower the affinity of the organic solvent with the styrene tar and, at the same time, heighten the affinity of the organic solvent with the phenolic polymerization inhibitor. As typical examples of the oxygen-containing organic solvent, there can be cited aliphatic alcohols such as methanol, ethanol, n-propanol, and isopropanol, ketones such as acetone, methylethyl ketone, and methylisobutyl ketone, ethers such as dioxane, and polyhydric alcohols such as ethylene glycol and glycerol. In the oxygen-containing organic solvents cited above, the aliphatic alcohols and the ketones are preferred and methanol is the most preferred. More specifically, methanol is only half as soluble in the styrene tar as is ethanol and twice as soluble in the polymerization inhibitor as ethanol. Moreover, methanol is advantageous in that it avoids forming an azeotrope with an aromatic hydrocarbon.

When this oxygen-containing organic solvent is contacted with the styrene tar which contains the phenolic polymerization inhibitor, the phenolic polymerization inhibitor in the styrene tar is extracted into the oxygen-containing organic solvent phase. When the mixture in which the extraction has taken place is left standing, there ensues separation of the styrene tar phase and the oxygen-containing organic solvent phase. Thus, two independent phases are obtained. For this purpose, the oxygen-containing organic solvent should be capable of dissolving the phenolic polymerization inhibitor, not exhibit a high affinity with the styrene polymer or oligomer as the main component of the styrene tar, and possess a specific gravity different from that of the styrene tar. For the purpose of improving the properties necessary for the fulfilment of the above requirements, the oxygen-containing organic solvent may have incorporated therein a polar solvent such as water. The amount of the oxygen-containing organic solvent to be used is in the range of about 50 to 1,000 parts by weight, preferably about 100 to 500 parts by weight, based on 100 parts by weight of the styrene tar, though this range varies more or less depending on the kind of the oxygen-containing organic solvent and the phenolic polymerization inhibitor content in the styrene tar. If the amount of the oxygen-containing organic solvent to be used is less than 100 parts by weight, the recovery ratio of the phenolic polymerization inhibitor is in sufficient. Conversely, if this amount exceeds 1,000 parts by weight, there is a disadvantage in that the recovery of the oxygen-containing organic solvent requires a large consumption of energy. It is advantageous to carry out the extraction in a multiple-stage apparatus or a counterflow apparatus, because the efficiency of the extraction is enhanced, the consumption of the oxygen-containing organic solvent is decreased, and the ratio of recovery is improved. During the course of the extraction, the temperature of the mixture desirably ranges between about 10° and 75° C., and preferably between about 20° and 70° C. The conditions for extraction are selected so that the ratio of recovery preferably rises above 80%.

Where the styrene tar and the oxygen-containing organic solvent phase are not easily separated, the separation may be facilitated by addition of water. The addition of water serves to make the phase boundary more pronounced and facilitate the separation. The addition of water is desirably made by mixing the oxygen-containing organic solvent with water prior to the extraction. The amount of water to be added is desirably in the range of about 5 to 200 parts by weight, preferably about 10 to 50 parts by weight based on 100 parts by weight of the oxygen-containing organic solvent, though this range is more or less variable with the kind of the solvent and the temperature of extraction, for example. If the amount of water so added exceeds about 200 parts by weight, the recovery ratio of the phenolic polymerization inhibitor is not sufficient. Conversely, if this amount is less than about 5 parts by weight, the added water is not as effective in making the phase boundary more pronounced, as expected. For example, when this amount is 5% by weight, 10% by weight, or 20% by weight, based on the amount of methanol, the extraction ratio in the first stage are 75%, 57%, and 46% respectively.

The oxygen-containing organic solvent phase is mixed with the aromatic hydrocarbon solvent. The aromatic hydrocarbon solvent is desirably an aromatic hydrocarbon which possesses a higher boiling point than the oxygen-containing organic solvent and has not more than 15 carbon atoms in the molecular unit thereof. Typical examples of aromatic hydrocarbons which fulfil this requirement are benzene, toluene, ethyl benzene, styrene, and dehydrogenated oil of ethyl benzene. Desirably, an aromatic hydrocarbon contained in the raw material subjected to distillation is used. Even more desirably, an aromatic hydrocarbon having a lower boiling point than styrene is used. Examples of an aromatic hydrocarbon which satisfies the above criteria include benzene, toluene, ethyl benzene, an a mixture of ethyl benzene as a main component thereof. The amount of the aromatic hydrocarbon solvent to be used is desirably more than the amount necessary for thorough dissolution of the polymerization inhibitor. Generally, this amount is in the range of about 0.2 to 5 parts by weight, preferably about 0.5 to 2 parts by weight, based on 1 part by weight of the styrene tar. When the resultant mixture tends to form an azeotrope, the aromatic hydrocarbon solvent must Le added in an excess amount. The amount of the aromatic hydrocarbon solvent is in the range of about 0.1 to 1.0 part by weight, based on 1 part by weight of the amount of the oxygen-containing organic solvent.

The mixture consequently obtained is subjected to distillation to induce separation of the mixture into a solution of the phenolic polymerization inhibitor in the aromatic hydrocarbon solvent and the oxygen-containing organic solvent. The distillation temperature is selected on the condition that the aromatic hydrocarbon to be used will remain and the oxygen-containing organic solvent will be distilled out at the temperature selected. Where ethyl benzene and methanol are used, for example, this temperature desirably falls in the range of about 60° to 110° C. What remains after the separation of the oxygen-containing organic solvent by distillation is a solution of the phenolic polymerization inhibitor in the aromatic hydrocarbon solvent. When a polar solvent such as water has been added during the course of the extraction, the solution resulting from the distillation might contain the polar solvent. This polar solvent may be removed by such means as phase separation.

The solution of the phenolic polymerization inhibitor in the aromatic hydrocarbon solvent may be used in its unmodified form as part or whole of the polymerization inhibitor for a vinyl aromatic compound. In other words, it can be added to the raw material containing the vinyl aromatic compound desired to be distilled. One example of the material containing the vinyl aromatic compound to be distilled is a crude styrene distillation residue obtained during the distillation of a dehydrogenated oil of ethyl benzene. The oxygen-containing organic solvent which has been distilled out may be circulated to the extraction stage. In this case, water and/or part of the aromatic hydrocarbon solvent is generally distilled out. Water and the aromatic hydrocarbon are sometimes distilled off but may be left unremoved when the amount is small.

Continuous operation of the method of this invention is described below with reference to FIG. 1.

The styrene tar containing the phenolic polymerization inhibitor which is formed in the distillation of a dehydrogenated oil of ethyl benzene (not shown) is forwarded through a conduit 1 to a extractor 2 and the oxygen-containing organic solvent is forwarded through a conduit 3 to the extractor 2. To this extractor 2, part or whole of the oxygen-containing organic solvent (possibly containing the aromatic hydrocarbon solvent and/or water) separated in a second distillation column 4 is forwarded through a conduit 5 and part or whole of the water separated in a separator 6 is forwarded through a conduit 7. In this extractor 2, the solvent introduced through the lower part thereof and the styrene tar containing polymerization inhibitor introduced through the upper part thereof are brought into countercurrent contact at a multiplicity of stages and the heavy styrene tar is discharged through the lower part and the light solvent phase is discharged through the upper part. The polymerization inhibitor is extracted into the oxygen-containing organic solvent phase which forms an upper layer. The styrene tar phase (having a minor amount of the oxygen-containing organic solvent dissolved therein) forms a lower layer. The styrene tar phase which forms the lower layer is forwarded through a conduit 8 to a first distillation column 9. From the bottom of this distillation column, the styrene tar is discharged through a conduit 10. From the top of this distillation column, the oxygen-containing organic solvent (containing the aromatic hydrocarbon) is separated. This oxygen-containing organic solvent may be recycled to the extraction stage or to the second distillation stage. Since it generally contains the aromatic hydrocarbon, it is desirably returned to the second distillation column 4.

The oxygen-containing organic solvent phase containing the polymerization inhibitor and forming the upper layer (where water is added, the phase is formed from a mixture of the organic solvent with water) is discharged through a conduit 13 and then mixed in a mixer 16 with the aromatic hydrocarbon solvent supplied through the conduit 12 and the oxygen-containing organic solvent introduced through the top of the first distillation column 9. The resultant mixture is introduced into the second distillation column 4.

In the second distillation column 4, the oxygen-containing organic solvent and the azeotrope which is formed between the oxygen-containing organic solvent and a minor amount of water and/or the aromatic hydrocarbon solvent is separated through the top. A portion or the whole of the discharged the oxygen-containing organic solvent is circulated to the extractor 2 through the conduit 5. In the meanwhile, the bottoms which contain the aromatic hydrocarbon solvent having dissolved therein the polymerization inhibitor (possibly containing water where water has been used as a polar solvent) are forwarded through the conduit 14 to the separator 6 so as to effect expulsion of water. In the separator the bottom liquid is separated into two layers. The water phase forming a lower layer is partly or wholly circulated through the conduit 7 to the extractor 2. The solution of the polymerization inhibitor in the aromatic hydrocarbon solvent which forms an upper layer is discharged through the conduit 15 (through the conduit 14 when it contains water) and circulated in its unmodified form to the stage for distillation of the dehydrogenated oil of ethyl benzene. Otherwise, it is subjected to distillation, when necessary, for concentration of the polymerization inhibitor.

Now, the method of this invention will be described more specifically below with reference to working examples. All the parts and percents mentioned in the working examples are expressed by weight unless specified otherwise.

EXAMPLES 1 to 7

A mixture of the oxygen-containing organic solvents indicated in Table 1 with water and a styrene distillation residue (comprising 5.7% by weight of styrene and the balance of a heavy substance such as polymer) obtained during the distillation of dehydrogenated oil of ethyl benzene containing 2,4-dinitrophenol (DNP) as a polymerization inhibitor were contacted in the ratios shown in Table 1 by stirring for 10 minutes and the resultant mixture was left standing for 2 to 3 minutes. Consequently, the mixture was separated into an oxygen-containing organic solvent phase and a styrene residue phase. Then, the oxygen-containing organic solvent phase and ethyl benzene added thereto were mixed and subjected to distillation to separate into the mixture a solution of 2,4-dinitrophenol in ethyl benzene and the oxygen-containing organic solvent. In this case, the final distillation temperature was 100° C. The ethyl benzene solution of 2,4-dinitrophenol was left standing at a lowered temperature to effect separation of the ethyl benzene solution of 2,4-dinitrophenol from water. The conditions of the treatment and the results are shown in Table 1.

EXAMPLES 8 to 14

Removal of the polymerization inhibitor was carried out by following the procedure of Example 1, except that the extraction with the oxygen-containing organic solvent was performed twice. The conditions and the results are shown in Table 2.

TABLE 1

| | Extraction conditions | | | | | Results of extraction Amount of | Distillation conditions | Results of distillation | | |
|---|---|---|---|---|---|---|---|---|---|---|
| | Styrene residue | | Oxygen-containing organic solvent | | Water | Temperature | oxygen-containing organic solvent phase | Amount of ethyl benzene added | DNP-EB solution | | Ratio of recovery of DNP |
| Example | Amount (parts) | DNP content (%) | Kind | Amount (parts) | Amount (parts) | (°C.) | (parts) | (parts) | Amount (parts) | DNP concentration (%) | (%) |
| 1 | 100 | 2.47 | aceton | 300 | 300 | 35 | 570.5 | 170 | 211.6 | 0.43 | 36.9 |
| 2 | 100 | 2.47 | aceton | 500 | 500 | 50 | 328.0 | 100 | 122.3 | 0.99 | 48.9 |
| 3 | 100 | 2.33 | methanol | 300 | 500 | 15 | 805.5 | 240 | 298.7 | 0.14 | 18.1 |
| 4 | 100 | 2.47 | methanol | 500 | 200 | 30 | 713.5 | 210 | 263.9 | 0.61 | 65.6 |
| 5 | 100 | 2.47 | ethanol | 300 | 100 | 50 | 422.5 | 130 | 158.1 | 0.90 | 57.8 |
| 6 | 100 | 2.33 | ethanol | 500 | 300 | 15 | 812.5 | 240 | 300.7 | 0.51 | 66.2 |

TABLE 1-continued

| | Extraction conditions | | | | | Results of extraction Amount of | Distillation conditions | Results of distillation | | Ratio of recovery of DNP (%) |
|---|---|---|---|---|---|---|---|---|---|---|
| | Styrene residue | | Oxygen-containing organic solvent | | Water | Temper- | oxygen-containing organic | Amount of ethyl | DNP-EB solution | | |
| Example | Amount (parts) | DNP content (%) | Kind | Amount (parts) | Amount (parts) | ature (°C.) | solvent phase (parts) | benzene added (parts) | Amount (parts) | DNP concen- tration (%) | |
| 7 | 100 | 2.47 | ethanol | 250 | 100 | 15 | 303.6 | 130 | 151.1 | 0.9.0 | 54.8 |

DNP: 2,4-Dinitrophenol
EB: Ethyl benzene

TABLE 2

| | Extraction conditions | | | | | | | Results of extraction Amount of oxygen-containing organic solvent phase (parts) | Distil- lation condi- tions Amount of ethyl benzene added (parts) | Results of distillation | | Ratio of recovery of DNP (%) |
|---|---|---|---|---|---|---|---|---|---|---|---|---|
| | Styrenes residue* | | Num- ber of ex- trac- tion | Oxygen- containing organic solvent* | | Water* | Tem- per- ature (°C.) | | | DNP-EB solution | | |
| Exam- ple | Amount (parts) | DNP con- tent (%) | | Kind | Amount (parts) | Amount (parts) | | | | Amount (parts) | DNP concen- tration (%) | |
| 8 | 100 | 2.47 | 2 | methanol | 100 | 100 | 15 | 301.1 | 90 | 130.4 | 0.61 | 32.4 |
| 9 | 100 | 2.47 | 2 | methanol | 150 | 100 | 15 | 404.8 | 120 | 174.9 | 0.77 | 54.8 |
| 10 | 100 | 2.47 | 2 | methanol | 200 | 100 | 15 | 511.1 | 150 | 220.4 | 0.72 | 64.4 |
| 11 | 100 | 2.47 | 2 | methanol | 250 | 100 | 15 | 918.2 | 260 | 392.7 | 0.43 | 68.6 |
| 12 | 100 | 2.47 | 2 | ethanol | 100 | 100 | 15 | 305.8 | 90 | 131.9 | 0.97 | 52.0 |
| 13 | 100 | 2.47 | 2 | ethanol | 150 | 100 | 15 | 606.6 | 177 | 258.9 | 0.59 | 62.2 |
| 14 | 100 | 2.47 | 2 | ethanol | 200 | 100 | 15 | 522.6 | 150 | 224.2 | 0.77 | 69.6 |

*per one extraction

EXAMPLE 15

In an apparatus constructed as illustrated in FIG. 1, 100 parts/hr of a 2,4-dinitrophenol-containing styrene distillation residue (comprising 6.0% of 2,4-dinitrophenol, 5.7% of styrene, and the balance of heavy substances) formed in the stage for distillation of dehydrogenated ethyl benzene was introduced into a extractor 2 having a theoretical number of stages of 6.5 through the top thereof. A mixture of 0.64 part/hr of freshly supplied methanol 3, 161.6 parts/hr of the methanol (containing 7.5% of ethyl benzene) circulated from the second distillation column 4, and 28.5 parts/hr of water circulated from the separator 6was introduced therein through the bottom thereof. The top and bottom feeds were contacted by stirring in a multiplicity of stages to effect thorough contact and extraction of 2,4-dinitrophenol. The extraction temperature was kept in the range of 50° to 60° C. and the retention time of the styrene tar was about 8 seconds. Into the distillation column 4, 211 parts/hr of the methanol phase (comprising 3.4% of 2,4-din&trophenol, 11.3% of water, 2.2% of ethyl benzene, 1.8% of styrene, 10.0% of heavy substances, and the balance of methanol) was introduced. From this extractor 2, 79.8 parts/hr of a styrene distillation residue (comprising 0.6% of 2,4-dinitrophenol, 3.4% of methanol, 9.3% of ethyl benzene, 2.4% of styrene, and the balance of heavy substance) was discharged through one bottom.

The styrene distillation residue phase was supplied to the first distillation column 9 to be separated by distillation into 69.8 parts/hr of the styrenes distillation residue (comprising 2.0% of ethyl benzene, 1.1% of styrene, 0.7% of 2,4-dinitrophenol, and the balance of heavy substances) and 9.8 parts/hr of the first distillate (comprising 27.0% of methanol, 11.7% of styrene, and the balance of ethyl benzene). In this case, the column top temperature was 62.1° C. and the column bottom temperature was 125.3°±40° C.

The methanol phase was mixed with 81.7 parts/hr of ethyl benzene and 9.88 parts/hr of the (first distillate and the resultant mixture was supplied to the second distillation column 4 to be separated therein by distillation into 161.6 parts/hr of the second distillate (comprising 92.5% of methanol and 7.5% of ethyl benzene) and 140.3 parts/hr of a water-containing ethyl benzene solution of 2,4-dinitrophenol (comprising 5.3% of 2,4-dinitrophenol, 2.4% of methanol, 11.0% of water, 56.8% of ethyl benzene, 3.% of styrene, and the balance of heavy substances). In this case, the column 4 top temperature was 65.9° C. and the column bottom temperature was 87.8° C.

The second distillate having methanol as a main component was circulated to the extractor 2 for reuse and 140.3 parts/hr of the water-containing ethyl benzene solution of 2,4-dinitrophenol discharged from the column bottom was left standing in the separator 6 at a lowered temperature to be separated into 28.5 parts/hr of the circulation water (comprising 6.4% of 2,4-dinitrophenol, 9.4% of methanol, 0.3% of ethyl benzene, and the balance of water) and 111.8 parts/hr of the ethyl benzene solution of 2,4-dinitrophenol (comprising 5.0% of 2,4-dinitrophenol, 0.6% of methanol, 71.2% of ethyl benzene, 4.5% of styrene, and the balance of heavy substances). The circulation water was circulated to the extractor 2 for reuse and the ethyl benzene solution of 2,4-dinitrophenol was used as a polymerization inhibitor for styrene as set forth in the following example wherein the recovery ratio of 2,4-dinitrophenol was 92.1%.

A mixture containing 100 parts of dehydrogenated oil of ethyl benzene (comprising 0.67% of benzene, 2.25% of toluene, 24.45% of ethyl benzene, and 61.98% of styrene), $4.2 \times 10^{-3}$ part of 2,4-dinitrophenol, and $4.36 \times 10^{-1}$ part of the recovered ethyl benzene solution of 2,4-dinitrophenol (containing $2.18 \times 10^{-2}$ part of 2,4-dinitrophenol) as a polymerization inhibitor was supplied to the distillation stage using three distillation columns to be distilled therein. The light fractions of benzene and toluene were separated from the first distillation column through the top thereof, the ethyl benzene fraction was removed from the second distillation column through the top thereof, and styrene was recovered from the third distillation column through the top thereof. The amount of the styrene tar which remained after the separation of styrene was 0.68 part.

What is claimed is:

1. A method for the recovery of a phenolic polymerization inhibitor from a styrene distillation residue containing said phenolic polymerization inhibitor, which method comprises extracting said inhibitor from said styrene distillation residue with an oxygen-containing organic solvent having not more than 6 carbon atoms to form an oxygen-containing organic solvent phase, adding an aromatic hydrocarbon solvent to said oxygen-containing organic solvent phase to form a mixture, and subjecting said mixture to distillation thereby separating said mixture into a solution of said phenolic polymerization inhibition in said aromatic hydrocarbon solvent and said oxygen-containing organic solvent.

2. The method according to claim 1, wherein said oxygen-containing organic solvent is an aliphatic alcohol or a ketone having not more than 5 carbon atoms.

3. The method according to claim 1, wherein the amount of said oxygen-containing organic solvent to be used is in the range of about 50 to 1,000 parts by weight, based on 100 parts by weight of said styrene distillation residue.

4. The method according to claim 1, wherein the amount of said aromatic hydrocarbon solvent to be used is in the range of about 0.2 to 5 parts by weight, based on 1 part by weight of said styrene distillation residue.

5. The method according to claim 1, wherein the amount of said aromatic hydrocarbon solvent is in the range of about 0.1 to 1.0 part by weight, based on 1 part by weight of said oxygen-containing organic solvent.

6. The method according to claim 2, wherein said oxygen-containing organic solvent is selected from the group consisting of acetone, methanol, and ethanol.

7. The method according to claim 2, wherein said phenolic polymerization inhibitor is a nitrophenol.

8. The method according to claim 7, wherein said nitrophenol is a dinitrophenol.

9. The method according to claim 7, wherein said nitrophenol is a mononitrophenol.

10. The method according to claim 1, wherein said aromatic hydrocarbon has not more than 15 carbon atoms in the molecular unit thereof.

11. The method according to claim 10, wherein said aromatic hydrocarbon solvent is at least one member selected from the group consisting of benzene, toluene, ethyl benzene, styrene, and dehydrogenated oil of ethyl benzene.

12. The method according to claim 11, wherein said aromatic hydrocarbon solvent has ethyl benzene as a main component thereof.

13. The method according to claim 1, wherein the extraction temperature is in the range of about 10° to 75° C.

14. The method according to claim 1, wherein the step of extracting the phenolic polymerization inhibitor from said styrene distillation residue with the oxygen-containing organic solvent is carried out in the presence of water.

15. The method according to claim 14, wherein the amount of water is in the range of about 5 to 200 parts by weight, based on 100 part by weight of the oxygen-containing organic solvent.

16. A method for the recovery of a phenolic polymerization inhibitor from a styrene distillation residue containing said phenolic polymerization inhibitor, which method comprises supplying said styrene distillation residue, an oxygen-containing organic solvent having not more than 6 carbons atoms, and water to a extractor thereby extracting said phenolic polymerization inhibitor with said oxygen-containing organic solvent phase, adding an aromatic hydrocarbon solvent to the separated oxygen-containing organic solvent phase, subjecting the resultant mixture to distillation thereby effecting separation of said oxygen-containing organic solvent and solution of the inhibitor in said aromatic hydrocarbon, and separating water from the remaining aromatic hydrocarbon solution.

17. The method according to claim 16, further comprising circulating the oxygen-containing organic solvent separated in the stage of distillation to said extractor.

18. The method according to claim 17, wherein at least a portion of the water supplied to said extractor is the water separated from the remaining aromatic hydrocarbon solution in the stage of separation.

19. The method according to claim 16 further comprising further distilling, wherein the solution containing the styrene distillation residue and forming a lower layer in the extractor is further distilled for separation of the solvent and mixing the solvent so separated with the solution of said phenolic polymerization inhibitor in the oxygen-containing organic solvent separated in the extractor.

* * * * *